United States Patent [19]

Förster et al.

[11] Patent Number: 5,090,991
[45] Date of Patent: Feb. 25, 1992

[54] HERBICIDAL N-ISOPROPYLHETEROARYLOX-YACETANILIDES

[75] Inventors: Heinz Förster, Wuppertal; Roland Andree, Langenfeld; Hans-Joachim Santel, Leverkusen; Robert R. Schmidt, Bergisch Gladbach; Harry Strang, Duesseldorf, all of Fed. Rep. of Germany

[73] Assignee: Bayer Akatiengesellschaft, Leverkusen, Fed. Rep. of Germany

[21] Appl. No.: 569,880

[22] Filed: Aug. 20, 1990

Related U.S. Application Data

[62] Division of Ser. No. 366,577, Jun. 15, 1989, Pat. No. 4,968,342.

[30] Foreign Application Priority Data

Jun. 27, 1988 [DE] Fed. Rep. of Germany ....... 3821600

[51] Int. Cl.$^5$ ................... C07D 280/08; A01N 43/82
[52] U.S. Cl. ......................... 71/90; 548/129; 548/130
[58] Field of Search ............... 548/129, 130; 71/90

[56] References Cited

U.S. PATENT DOCUMENTS 4,549,899  10/1985  Forster ............................. 548/129
4,756,741   7/1988  Forster ............................. 548/129

FOREIGN PATENT DOCUMENTS 300344  1/1989  European Pat. Off. ............ 548/129

*Primary Examiner*—Robert Gerstl
*Attorney, Agent, or Firm*—Sprung Horn Kramer & Woods

[57] ABSTRACT

Herbicidal N-isopropylheteroaryloxyacetanilides of the formula

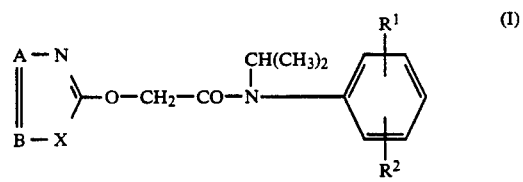

in which
A stands for nitrogen or the group C-$R^3$ where
$R^3$ stands for halogen, cyano, alkyl, halogenoalkyl, alkoxy, halogenoalkoxy, alkylthio, halogenoalkylthio, alkylsulphinyl or alkylsulphonyl,
B stands for nitrogen or the group C-$R^4$ where
$R^4$ stands for halogen, cyano, alkyl, halogenoalkyl, alkoxy, halogenoalkoxy, alkylthio, halogenolakylthio, alkylsulphinyl, halogenoalkylsulphinyl, alkylsulphonyl, halogenoalkylsulphonyl, for phenyl which is optionally substituted by halogen, alkyl, halogenoalkyl, alkoxy or halogenoalkoxy, or for the group -C$Y_2$-Z-$R^5$ where
$R^5$ stands for alkyl, which is optionally substituted by halogen, alkoxy or alkylthio, or for phenyl which is optionally substituted by halogen, alkyl, halogenoalkyl, alkoxy, halogenoalkoxy, alkylthio or halogenoalkylthio,
Y stands for hydrogen or halogen,
Z stands for oxygen, sulphur, SO or $SO_2$,
$R^1$ stands for hydrogen, halogen, cyano, nitro, alkyl, halogenoalkyl, alkoxy, halogenoalkoxy, alkylthio or halogenoalkylthio,
$R^2$ stands for hydrogen, halogen, alkyl, halogenoalkyl or alkoxy and
X stands for oxygen or sulphur, excluding the compound N-isopropyl-(5-trifluoromethyl-1,3,4-thiadiazol-2-yl)-oxyacetanilide.

10 Claims, No Drawings

HERBICIDAL N-ISOPROPYLHETEROARYLOXYACETANILIDES

This is a division of application Ser. No. 366,577, filed June 15, 1989, now U.S. Pat. No. 4,968,342.

The invention relates to novel N-isopropylheteroaryloxyacetanilides, a process for their preparation and their use of herbicides.

It has already been disclosed that certain heteroaryloxyacetanilides, such as, for example, N-methyl-2-(5-chloro-1,3,4-thiadiazol-2-yl-oxy)-acetanilide, exhibit herbicidal properties (cf. EP-A 192,117). However, the tolerance by crop plants of this known compound is not always completely satisfactory. -N-isopropyl-(5-trifluoromethyl-1,3,4-thiadiazol-2-yl)-oxyacetanilide has also been disclosed (cf. DE-A 3218482; EP-A 94,541; U.S. Pat. No. 4,585,471).

Novel N-isopropylheteroaryloxyacetanilides of the general formula (I)

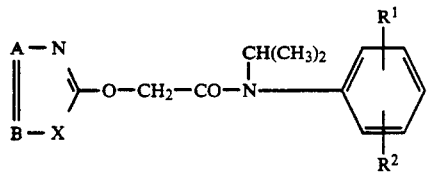  (I)

in which
  A stands for nitrogen or the group C-R³ where
  R³ stands for halogen, cyano, alkyl, halogenoalkyl, alkoxy, halogenoalkoxy, alklythio, halogenoalkylthio, alkylsulphinyl or alkylsulphonyl,
  B stands for nitrogen or the group C-R⁴ where
  R⁴ stands for halogen, cyano, alkyl, halogenoalkyl, alkoxy, halogenoalkoxy, alkylthio, halogenoalkylthio, alkylsulphinyl, halogenoalkylsulphinyl, alkylsulphonyl, halogenoalkylsulphonyl, for phenyl which is optionally substituted by halogen, alkyl, halogenoalkyl, alkoxy or halogenoalkoxy, or for the group -CY₂-Z-R⁵ where
  R⁵ stands for alkyl, which is optionally substituted by halogen, alkoxy or alkylthio, or for phenyl which is optionally substituted by halogen, alkyl, halogenoalkyl, alkoxy, halogenoalkoxy, alkylthio or halogenoalkylthio,
  Y stands for hydrogen or halogen,
  Z stands for oxygen, sulphur, SO or SO₂,
  R¹ stands for hydrogen, halogen, cyano, nitro, alkyl, halogenoalkyl, alkoxy, halogenoalkoxy, alkylthio or halogenoalkylthio,
  R² stands for hydrogen, halogen, alkyl, halogenoalkyl or alkoxy and
  X stands for oxygen or sulphur,
excluding the compound N-isopropyl-(5-trifluoromethyl-1,3,4-thiadiazol-2-yl)-oxyacetanilide, have now been found.

Furthermore, it has been found that the novel N-isopropylheteroaryloxyacetanilides of the general formula (I) are obtained when heteroarenes of the general formula (II)

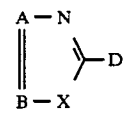  (II)

in which
  A, B and X have the abovementioned meanings and
  D stands for a nucleofugic leaving group,
are reacted with N-isopropylhydroxyacetanilides of the general formula (III)

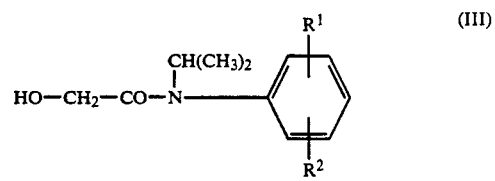  (III)

in which
  R¹ and R² have the abovementioned meanings,
  if appropriate in the presence of a diluent, if appropriate
  in the presence of an acid-binding agent and if appropriate
  in the presence of a catalyst.

Finally, it has been found that the novel N-isopropylheteroaryloxyacetanilides of the general formula (I) possess interesting herbicidal properties.

Surprisingly, the novel N-isopropylheteroaryloxyacetanilides of the general formula (I) show considerably better selective properties than N-methyl-2-(5-chloro-1,3,4-thiadiazl-2-yl-oxy)-acetanilide, which is known while having a powerful herbicidal action.

The invention preferably relates to compounds of the formula (I) in which
  A stands for nitrogen or the group C-R³, where
  R³ stands for fluorine, chlorine, bromine, cyano, for C₁-C₄-alkyl which is optionally substituted by fluorine and/or chlorine, for C₁-C₄-alkoxy which is optionally substituted by fluorine and/or chlorine, for C₁-C₄-alkylthio which is optionally substituted by flourine and/or chlorine, for C₁-C₄-alkylsulphinyl or C₁-C₄-alkylsulphonyl,
  B stands for nitrogen or the group C-R⁴ where
  R⁴ stands for fluorine, chlorine, bromine, cyano, for C₁-C₄-alkyl which is optionally substituted by fluorine and/or chlorine, for C₁-C₄-alkoxy which is optionally substituted by fluorine and/or chlorine, for C₁-C₄-alkylthio which is optionally substituted by fluorine and/or chlorine, for C₁-C₄-alkylsulphinyl which is optionally substituted by fluorine and/or chlorine, for C₁-C₄-alkylsulphonyl which is optionally substituted by fluorine and/or chlorine, for phenyl which is optionally substituted by fluorine, chlorine, bromine, C₁-C₄-alkyl, trifluoromethyl, C₁-C₄-alkoxy or trifluoromethoxy, or for the group -CY₂-Z-R⁵ where
  R⁵ stands for C₁-C₄-alkyl which is optionally substituted by fluorine and/or chlorine, C₁-C₄-alkoxy or C₁-C₄-alkylthio, or for phenyl which is optionally substituted by fluorine, chlorine, bromine, C₁-C₄-alkyl, trifluoromethyl, C₁-C₄-alkoxy, trifluoromethoxy, C₁-C₄-alkylthio or trifluoromethylthio,
  Y stands for hydrogen, fluorine or chlorine,
  Z stands for oxygen, sulphur, SO or SO₂, $R^1$ stands for hydrogen, fluorine, chlorine, bromine, cyano, nitro, for $C_1$-$C_4$-alkyl which is optionally substituted by fluorine and/or chlorine, for $C_1$-$C_4$-alkoxy which is optionally substituted by fluroine and/or chlorine, or for $C_1$-$C_4$-alkylthio which is optionally substituted by fluorine and/or chlorine, $R^2$ stands for hydrogen, fluorine, chlorine, bromine, methyl, trifluoromethyl or methoxy and X stands for oxygen or sulphur, excluding the compound N-isopropyl-(5-trifluoromethyl-1,3,4-thiadiazol-2-yl)-oxyacetanilide.

A very particularly preferred group of compounds of the formula (I) are those of the formula (Ia)

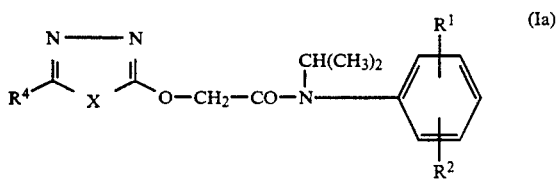

in which $R^1$ stands for hydrogen, fluorine, chlorine, methyl, trifluoromethyl or methoxy, $R^2$ stands for hydrogen, $R^4$ stands for chlorine, trifluoromethyl, chlorodifluoromethyl, fluorodichloromethyl, dichloromethyl, trichloromethyl, pentafluoroethyl, heptafluoropropyl, methylthio, ethylthio, propylthio, methylsulphinyl, ethylsulphinyl, propylsulphinyl, methylsulphonyl, ethylsulphonyl, propylsulphonyl or phenyl and X stands for oxygen or sulphur, excluding the compound N-isopropyl-(5-trifluoromethyl-1,3,4-thiadiazol-2-yl)-oxyacetanilide.

A further particularly preferred group of compounds of the formula (I) are those of the formula (Ib)

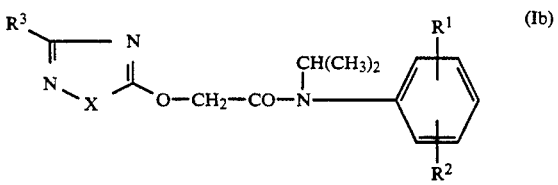

in which $R^1$ stands for hydrogen, fluorine, chlorine, methyl, trifluoromethyl or methoxy, $R^2$ stands for hydrogen, $R^3$ stands for chlorine, difluoromethyl, trifluoromethyl, chlorodifluoromethyl, fluorodichloromethyl, dichloromethyl, trichloromethyl, methyl, ethyl, propyl, isopropyl, methylthio, ethylthio, propylthio, methylsulphonyl, ethylsulphonyl, propylsulphonyl, methylsulphinyl, ethylsulphinyl or propylsulphinyl and X stands for oxygen or sulphur.

A third particularly preferred group of compounds of the formula (I) are those of the formula (Ic)

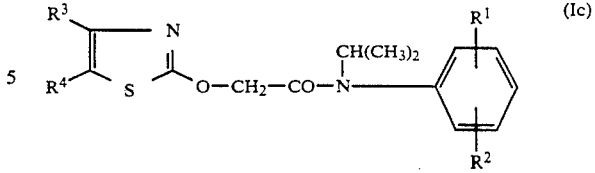

in which $R^1$ stands for hydrogen, fluorine, chlorine, methyl, trifluoromethyl or methoxy, $R^2$ stands for hydrogen, $R^3$ stands for chlorine, fluorine, methyl, difluoromethyl, dichloromethyl, chlorodifluoromethyl, fluorodichloromethyl, trichloromethyl or trifluoromethyl and $R^4$ stands for chlorine, cyano, difluoromethyl, dichloromethyl, chlorodifluoromethyl, fluorodichloromethyl, trichloromethyl or trifluoromethyl.

Examples of the compounds of the formula (I) are listed in Table 1 below. -cf. also the Preparation Examples.

TABLE 1

Examples of the compounds of the formula (I)

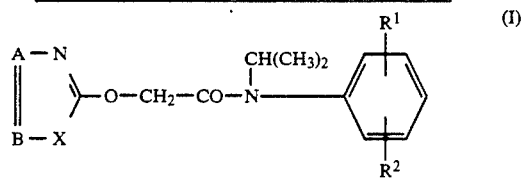

| A | B | X | $R^1$ | $R^2$ |
|---|---|---|-------|-------|
| N | C—Cl | S | H | H |
| N | C—Cl | S | 4-F | H |
| N | C—Cl | S | 2-Cl | H |
| N | C—Cl | S | 3-Cl | H |
| N | C—Cl | S | 4-Cl | H |
| N | C—Cl | S | 3-CH$_3$ | H |
| N | C—Cl | S | 4-CH$_3$ | H |
| N | C—Cl | S | 4-OCH$_3$ | H |
| N | C—CF$_3$ | S | 2-F | H |
| N | C—CF$_3$ | S | 4-F | H |
| N | C—CF$_3$ | S | 2-Cl | H |
| N | C—CF$_3$ | S | 3-Cl | H |
| N | C—CF$_3$ | S | 4-Cl | H |
| N | C—CF$_3$ | S | 3-CH$_3$ | H |
| N | C—CF$_3$ | S | 4-CH$_3$ | H |
| N | C—CF$_3$ | S | 4-OCH$_3$ | H |
| N | C—CF$_2$Cl | S | H | H |
| N | C—CFCl$_2$ | S | H | H |
| N | C—CHCl$_2$ | S | H | H |
| N | C—CCl$_3$ | S | H | H |
| N | C—C$_2$F$_5$ | S | H | H |
| N | C—C$_3$F$_7$ | S | H | H |
| N | C—SCH$_3$ | S | H | H |
| N | C—SOCH$_3$ | S | H | H |
| N | C—SO$_2$CH$_3$ | S | H | H |
| C—Cl | N | O | H | H |
| C—Cl | N | S | H | H |
| C—Cl | N | S | 2-Cl | H |
| C—Cl | N | S | 3-Cl | H |
| C—Cl | N | S | 4-Cl | H |
| C—CHF$_2$ | N | S | H | H |
| C—CF$_3$ | N | S | H | H |
| C—CCl$_2$F | N | S | H | H |
| C—CF$_2$Cl | N | S | H | H |
| C—CHCl$_2$ | N | S | H | H |
| C—CCl$_3$ | N | S | H | H |
| C—CH$_3$ | N | S | H | H |
| C—C$_2$H$_5$ | N | S | H | H |
| C—C$_3$H$_7$ | N | S | H | H |
| C—CH(CH$_3$)$_2$ | N | S | H | H |
| C—SCH$_3$ | N | S | H | H |

TABLE 1-continued

Examples of the compounds of the formula (I)

$$\begin{array}{c} \text{A—N} \\ \phantom{\text{A—}}\Vert \\ \text{B—X} \end{array}\!\!\!\!\!\!\!\!\!\!\!\!\!\!\!\!\!\!\!\!\!\!\!\!\!\!\!\!\!\!\!\!\!\!\!\!\!\!\text{—O—CH}_2\text{—CO—N}\underset{\underset{\text{R}^2}{|}}{\overset{\overset{\text{CH(CH}_3)_2}{|}}{\phantom{\text{—}}}}\!\!\!\!\!\!\!\!\!\!\!\!\!\!\!\!\!\!\!\!\!\!\!\!\!\!\!\!\!\!\!\!\text{—}\!\!\bigcirc$$  (I)

| A | B | X | R¹ | R² |
|---|---|---|----|----|
| C—SC₂H₅ | N | S | H | H |
| C—SC₃H₇ | N | S | H | H |
| C—SOCH₃ | N | S | H | H |
| C—SOC₂H₅ | N | S | H | H |
| C—SOC₃H₇ | N | S | H | H |
| C—SO₂CH₃ | N | S | H | H |
| C—SO₂C₂H₅ | N | S | H | H |
| C—SO₂C₃H₇ | N | S | H | H |
| C—Cl | C—Cl | S | H | H |
| C—Cl | C—Cl | S | 4-F | H |
| C—Cl | C—Cl | S | 2-Cl | H |
| C—Cl | C—Cl | S | 3-Cl | H |
| C—Cl | C—Cl | S | 4-Cl | H |
| C—Cl | C—Cl | S | 3-CH₃ | H |
| C—Cl | C—Cl | S | 4-CH₃ | H |
| C—Cl | C—Cl | S | 4-OCH₃ | H |
| C—Cl | C—CN | S | H | H |
| C—Cl | C—CHF₂ | S | H | H |
| C—Cl | C—CHF₂ | S | 2-Cl | H |
| C—Cl | C—CHF₂ | S | 3-Cl | H |
| C—Cl | C—CHF₂ | S | 4-Cl | H |
| C—F | C—CHF₂ | S | H | H |
| C—F | C—CHF₂ | S | 2-Cl | H |
| C—F | C—CHF₂ | S | 3-Cl | H |
| C—F | C—CHF₂ | S | 4-Cl | H |
| C—CF₃ | C—CN | S | H | H |
| C—CF₃ | C—Cl | S | H | H |
| C—Cl | C—CF₃ | S | H | H |
| C—CH₃ | C—Cl | S | H | H |
| C—Cl | C—CF₂Cl | S | H | H |
| C—CH₃ | C—CN | S | H | H |
| N | C—CF₃ | S | 3-CF₃ | H |

If, for example, 2,4,5-trichlorothiazole and N-isopropylhydroxyacetanilide are used as starting substances, the course of the reaction in the process according to the invention may be represented by the following equation:

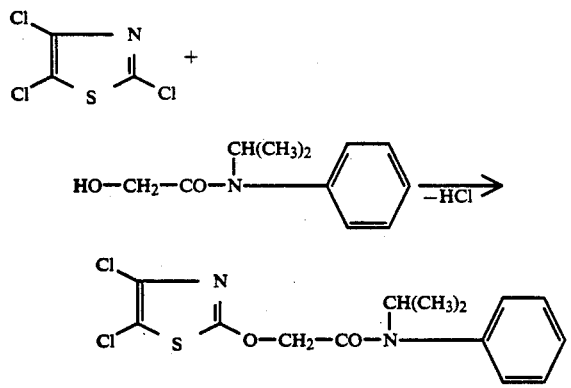

Formula (II) provides a general definition of the heteroarenes to be used as starting substances in the process according to the invention, for the preparation of compounds of the formula (I).

In formula (II), A, B and X preferably, or in particular, have those meanings which have already been mentioned above in connection with the description of the compounds of the formula (I) according to the invention as being preferred, or particularly preferred, for A, B and X, and D preferably stands for halogen or $C_1$–$C_4$-alkylsulphonyl, in particular for chlorine or methylsulphonyl.

Examples of the starting substances of the formula (II) which may be mentioned are: 2,4,5-trichlorothiazole, 2,4-dichloro-5-cyano-thiazole, 2,4-dichloro-5difluoromethyl-thiazole, 2,4-dichloro-5-dichloromethyl-thiazole, 2,4-dichloro-5-trichloromethylthiazole, 2-chloro-4-fluoro-5-difluoromethyl-thiazole, 2-chloro-4-fluoro-5-dichloromethyl-thiazole, 2-chloro-4-fluoro-5-trifluoromethyl-thiazole, 2-chloro-4-trifluoromethyl-5-cyano-thiazole, 2-chloro-4-methyl-5-cyano-thiazole, 2,4-dichloro-5-chlorodifluoromethyl-thiazole, 2,4-dichloro-5-fluoro-dichloromethyl-thiazole, 2,5-dichloro-4-methylthiazole, 2,5-dichloro-4-difluoromethyl-thiazole, 2,5-dichloro-4-trichloromethyl-thiazole, 2,5-dichloro-4-chlorodifluoromethyl-thiazole, 3,5-dichloro-1,2,4-thiadiazole, 3-difluoromethyl-5-chloro, 1,2,4-thiadiazole, 3-trifluoromethyl-5-chloro-1,2,4-thiadiazole, 3-chlorodifluoromethyl-5-chloro-1,2,4-thiadiazole, 3-fluorodichloromethyl-5-chloro-1,2,4-thiadiazole, 3-dichloromethyl-5chloro-1,2,4-thiadiazole, 3-trichloromethyl-5-chloro-1,2,4-thiadiazole, 3-methyl-5-chloro-1,2,4-thiadiazole, 3-methylthio-5-chloro-1,2,4-thiadiazole, 3-methylsulphinyl-5-chloro-1,2,4-thiadiazole, 3-methylsulphonyl-5-chloro-1,2,4-thiadiazole, 2,5-dichloro-1,3,4-thiadiazole, 2-chloro-5-methylsulphonyl-1,3,4-thiadiazole, 2-chloro-5-trifluoromethyl-1,3,4-thiadiazole, 2-methylsulphonyl-5-trifluoromethyl-1,3,4-thiadiazole, 2-chloro-5-chlorodifluoromethyl-1,3,4-thiadiazole, 2-chloro-5-fluorodichloromethyl-1,3,4-thiadiazole, 2-chloro-5-dichloromethyl-1,3,4-thiazole, 2-chloro-5-trichloromethyl-1,3,4-thiadiazole, 2-chloro-5-pentafluoroethyl-1,3,4-thiadiazole, 2-chloro-5heptafluoropropyl-1,3,4-thiadiazole, 2-chloro-5-methylthio-1,3,4-thiadiazole and 2-chloro-5-methyl-sulphinyl-1,3,4-thiadiazole.

The starting substances of the formula (II) are known and/or can be prepared by processes known per se (cf. U.S. Pat. No. 4,645,525 and literature quoted therein; J. Heterocycl. Chem. 11 (1974), 343–345; J. Org. Chem. 27 (1962), 2589–2592); DE-OS (German Published Specification) 3,422,861).

Formula (III) provides a general definition of the N-isopropylhydroxyacetanilides also to be used as starting substances in the process according to the invention.

In formula (III), $R^1$ and $R^2$ preferably, or in particular, have those meanings which have already been mentioned above in connection with the description of the compounds of the formula (I) according to the invention as being preferred, or particularly preferred, for $R^1$ and $R^2$.

Examples of the starting substances of the formula (III) which may be mentioned are: N-isopropylhydroxyacetanilide, 2'-fluoro-, 3'-fluoro-, 4'-fluoro-, 2'-chloro-, 3'-chloro-, 4'-chloro-, 3'-methyl-, 4'-methyl-, 3'-methoxy-, 4'-methoxy-, 3'-trifluoromethyl- and 4'-trifluoromethyl-N-isopropylhydroxyacetanilide.

The N-isopropylhydroxyacetanilides of the formula (III) are known and/or can be prepared by processes known per se (cf. U.S. Pat. No. 4,509,971 and U.S. Pat. No. 4,645,525; furthermore for U.S. Pat. No. 4,334,073, DE-A 3,038,598, DE-A 3,038,636, EP-A 37,526).

The process according to the invention for the preparation of the novel N-isopropylheteroaryloxyacetanilides of the formula (I) is preferably carried out using diluents. These preferably include hydrocarbons, such as, for example, toluene, xylene or cyclohexane, halogenohydrocarbons, such as, for example, methylene chloride, ethylene chloride, chloroform or chlorobenzene, ethers, such as, for example, diethyl ether, dipropyl ether, diisopropyl ether, dibutyl ether, diisobutyl ether, glycol dimethyl ether, tetrahydrofuran and dioxane, alcohols, such as, for example, methanol, ethanol, propanol, isopropanol or butanol, ketones, such as, for example, acetone, methyl ethyl ketone, methyl isopropyl ketone and methyl isobutyl ketone, esters, such as, for example, methyl acetate and ethyl acetate, amides, such as, for example, dimethylformamide, dimethylacetamide and N-methylpyrrolidone, nitriles, such as, for example, acetonitrile and propionitrile, sulphoxides, such as, for example, dimethyl sulphoxide, and also water or aqueous salt solutions.

Salts which can be used in this process preferably include chlorides or sulphates of alkali metal or alkaline earth metals, such as, for example, sodium chloride, potassium chloride or calcium chloride. Sodium chloride is particularly preferred.

The process according to the invention is preferably carried out using acid-binding agents. Acid-binding agents which are preferably used include strongly basic alkali metal compounds and alkaline earth metal compounds, for example oxides, such as, for example, sodium oxide, potassium oxide, magnesium oxide and calcium oxide, hydroxides, such as, for example, sodium hydroxide, potassium hydroxide, magnesium hydroxide and calcium hydroxide, and/or carbonates, such as, for example, sodium carbonate, potassium carbonate, magnesium carbonate and calcium carbonate.

The addition of 0.01 to 10% by weight (based on glycolamide employed, of the formula (III)) of a phase transfer catalyst may prove advantageous in some cases. Examples of such catalysts which may be mentioned are: tetrabutylammonium chloride, tetrabutylammonium bromide, tributyl-methylphosphonium bromide, trimethyl-$C_{13}/C_{15}$-alkyl-ammonium chloride, dibenzyl-dimethyl-ammonium methylsulphate, dimethyl-$C_{12}/C_{14}$-alkyl-benzylammonium chloride, tetrabutylammonium hydroxide, 18-crone-6, triethylbenzylammonium chloride, trimethylbenzylammonium chloride, tetraethylammonium bromide.

In the process according to the invention, the reaction temperatures can be varied in a relatively wide range. In general, the process is carried out at temperatures between $-50°$ C. and $+110°$ C., preferably at temperatures between $-20°$ C. and $+100°$ C.

The process according to the invention is generally carried out under atmospheric pressure, but it can also be carried out under increased or reduced pressure, for example between 0.1 and 10 bar.

For carrying out the process according to the invention, 0.5 to 5 moles, preferably 0.8 to 1.5 moles, of N-isopropylhydroxyacetanilide of the formula (III) are generally employed per mole of heteroarene of the formula (II). The reactants can be combined in an sequence. The reaction mixture is in each case stirred until the reaction is complete and worked up by customary methods.

The active compounds according to the invention can be used as defoliants, desiccants, agents for destroying broad-leaved plants and, especially, as weedkillers. By weeds, in the broadest sense, there are to be understood all plants which grown in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Impomoea, Polygonum, Sesbania, Ambrosia, Cirsium, Carduus, Sonchus, Salanum, Rorippa, Rotala, Lindernia, Lamium, Veronica, Abutilon, Emex, Datura, Viola, Galeopsis, Papaver and Centaurea.

Dicotyleodeon cultures of the genera: Gossypium, Glycine, Beta, Daucus, Phaseolus, Pisum, Solanum, Linum, Impomoea, Vicia, Nicotiana, Lycopersicon, Arachis, Brassica, Lactuca, Cucumis and Cucurbita.

Monocotyledon weeds of the genera: Echinochloa, Setaria, Panicum, Digitarin, Phleum, Poa, Festuca, Eleusine, Brachiaria, Lolium, Bromus, Avena, Cyperus, Sorghum, Agropyron, Cynodon, Monochloria, Fimbristylis, Sagittaria, Eleocharis, Scirpus, Paspalum, Ischaemum, Sphenoclea, Dactyloctenium, Argostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The compounds of the formula (I) according to the invention are particularly suitable for selectively combating monocotyledon weeds in monocotyledon and dicotyledon crops, especially using the pre-emergence method. They are particularly distinguished by being well tolerated by barley, wheat, corn rice, sunflowers and soya beans.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinate aromatics and chlorinate aliphatic hydrocarbons, such as chlorobenzenes, chloroethylenes or methylene chlorine, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and group natural minerals, such as kaolins, clays, talc, chalk, quartz, attapulgite, montmorillonite or diatomaceous earth, and ground synthetic minerals, such as highly disperse silica, alumin and silicates, as solid carriers for granules there are suitable: for example crushed and fractionated natural rocks such as calcite, marble, pumic, pepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkyl sulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices in the form of polymers, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, maganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

Suitable components for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N'-dimethyl-urea (METABENZTHIAZURON) for combating weeds in cereals; 4-amino-3-methyl-6-phenyl-1,2,4-traizin-5(4H)-one (METAMITRON) for combating weeds in sugar beets and 4-amino-6-(1,1-dimethylethyl-3-methylthio-1,2,4-5(4H)-one (METRIBUZIN) for combating weeds in soy beans; furthermore also 2-chloro-4-ethylamino-6-isopropylamino-1,3,5-triazine (ATRAZIN); methyl 2-[[[[[(4,6-dimethoxypyrimid-in-2-yl)amino]-carbonyl]-amino]-sulphonyl]-methyl]-benzoate (BENSULFURON); 5-amino-4-chloro-2-phenyl-2,3-dihydro-3-oxy-pyridazine (CHLORIDAZON); ethyl 2-{[(4-chloro-6-methoxy-2-pyrimidinyl)-aminocarbonyl]-aminosulphonyl}benzoate (CHLORIMURON); 2-chloro-N-{[(4-methoxy-6-methyl-1,3,5-traizin-2-yl)-amino]-carbonyl}-benzenesulphonamide (CHLORSULFURON); 2-chloro-4-ethylamino-6-(3-cyanopropylamino-1,3,5-triazine (CYANAZINE); 4-amino-6-t-butyl-3-ethylthio-1,2,4-traizin-5(4H)-one (ETHIOZIN); 1-methyl-3-phenyl-5-(3-trifluoromethyl-phenyl)-4-pyridone (FLURIDONE); 5-(2-chloro-4-trifluoromethyl-phenoxy)-N-methyl sulphonyl-2-nitrobenazamide (FOMESAFEN); methyl 2-[4,5-dihydro-4-methyl-4-(1-methylethyl)-5-oxo-1H-imidazol-2yl]-4(5)-methylbenzoate (IMAZAMETHABENZ); 2-[5-methyl-5-(1-methylethyl)- 4-oxo-2-imidazolin-2-yl]-3-quinolinecarboxylic acid (IMAQUIN); N-methyl-2-(1,3-benzothiazol-2-yloxy)-acetanilide (MEFENACET); 2-{[[((4-methoxy-6-methyl-1,3,5-triazin-2-yl)-emino-carbonyl]-emino]-sulphonyl}-benzoic acid or its methyl ester (METSULFURON); N-(1-ethylpropyl)-3,4-dimethyl-2,6dinitroaniline (PENDIMETHALIN); 2-chloro-4,6-bis-(ethylamino)-1,3,5-triazine (SIMAZIN); 2,4-bis-[N-ethylamino]-6-methylthio-1,3,5-triazine (SIMETRYNE); 4-ethylamino-2-tbutylamino-5-methylthio-s-triazine (TERBUTYRYNE); methyl 3-[[[[(4-methoxy-6methyl-1,3,5-triazin-2-yl)-amino]-carbonyl]-amino]-sulphonyl]-thiophene-2-carboxylate (THIAMETURON) and 2,6-dinitro-4-trifluoromethyl-N,N-dipropyaniline (TRIFLURALIN). Surprisingly, some mixtures also show synergistic action.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES

EXAMPLE 1

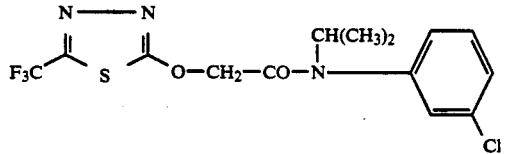

11.8 g (0.05 mol) of 2-methylsulphonyl-5-trifluoromethyl-1,3,4-thiadiazole are dissolved in 100 ml of acetone together with 11.4 g (0.05 mol) of 3'-chloro-N-isopropylhydroxyacetanilide. A solution of 2.4 gr of sodium hydroxide powder and 9 ml of water is slowly added dropwise at −20° C. Stirring is then continued at −20° C. for 3 hours, and the reaction mixture is then poured into water. The crystalline product is isolated by filtering off with suction.

16.1 g (85% of theory) of N-isopropyl-(5-tri-fluoromethyl-1,3,4-thiadiazol-2-yl)-3'-chloro-oxyacetanilide of refractive index $n_D^{20}$: 1.5170 are obtained.

The compounds of the formula (I) listed in Table 2 below can also be prepared analogously to Example 1 and following the general description of the preparation process according to the invention:

TABLE 2

Preparation Examples of the compounds of the formula (I)

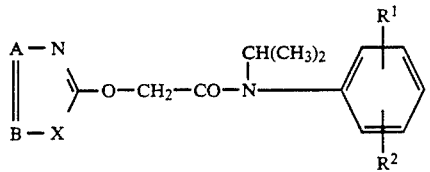

(I)

| Ex. No. | A | B | X | $R^1$ | $R^2$ | Melting point (°C./ refractive index) |
|---|---|---|---|---|---|---|
| 2 | N | C—Cl | S | H | H | 60 |
| 3 | N | C—CF$_3$ | S | 4-OCH$_3$ | H | $n_D^{20}$: 1.5165 |
| 4 | N | C—CF$_3$ | S | 4-CF$_3$ | H | |
| 5 | N | C—CF$_3$ | S | 4-Cl | H | 76 |
| 6 | N | C—CF$_3$ | S | 2-Cl | H | 81 |
| 7 | N | C—Cl | S | 3-Cl | H | 71 |
| 8 | N | C—Cl | S | 4-Cl | H | 88 |
| 9 | N | C—Cl | S | 2-Cl | H | $n_D^{20}$: 1.5645 |
| 10 | C—CF$_2$Cl | N | S | H | H | 66 |
| 11 | C—F | C—CHF$_2$ | S | H | H | 97 |
| 12 | N | C—C$_3$H$_7$ | S | H | H | $n_D^{20}$: 1.4730 |
| 13 | C—Cl | C—CN | S | H | H | 52 |
| 14 | C—CF$_3$ | C—CN | S | H | H | 91 |
| 15 | C—CCl$_2$F | N | S | H | H | |
| 16 | C—CCl$_3$ | N | S | H | H | 114 |
| 17 | C—Cl | N | O | H | H | 62 |
| 18 | C—Cl | C—CF$_3$ | S | H | H | 110 |
| 19 | C—SCH$_3$ | N | S | H | H | 136 |
| 20 | C—CH(CH$_3$)$_2$ | N | S | H | H | 45 |
| 21 | C—CH$_3$ | C—CN | S | H | H | 74 |
| 22 | C—Cl | C—Cl | S | H | H | $n_D^{20}$: 1.5529 |
| 23 | C—C$_3$H$_7$ | N | S | H | H | 31 |
| 24 | N | C—SO$_2$CH$_3$ | S | H | H | 133 |
| 25 | C—SO$_2$CH$_3$ | N | S | H | H | 82 |
| 26 | C—Cl | C—CHF$_2$ | S | H | H | 96 |
| 27 | C—CF$_3$ | N | S | H | H | 63 |
| 28 | C—SOCH$_3$ | N | S | H | H | |
| 29 | N | C—SC$_3$H$_7$ | S | H | H | 59 |
| 30 | N | C—phenyl | O | H | H | 157 |
| 31 | N | C—phenyl | O | 2-F | H | 172 |
| 32 | N | C—CF$_3$ | S | 3-F | H | 62 |
| 33 | N | C—CF$_3$ | S | 2-F | H | 89 |
| 34 | N | C—CF$_3$ | S | 4-F | H | 60 |
| 35 | N | C—CF$_3$ | S | 3-CH$_3$ | H | 86 |
| 36 | N | C—CF$_3$ | S | 3-CF$_3$ | H | 78 |
| 37 | N | C—CF$_3$ | S | 2-Cl | 4-Cl | 53 |
| 38 | N | C—CF$_3$ | S | 2-OCH$_3$ | H | 84 |
| 39 | N | C—Cl | S | 2-OCH$_3$ | H | 50 |
| 40 | C—Cl | C—CHF$_2$ | S | 2-OCH$_3$ | H | $n_D^{20}$: 1.5250 |
| 41 | N | C—Cl | S | 4-OC$_2$H$_5$ | H | 72 |
| 42 | N | C—CF$_3$ | S | 4-OC$_2$H$_5$ | H | $n_D^{20}$: 1.5040 |
| 43 | N | C—Cl | S | 4-SCH$_3$ | 3-Cl | 134 |
| 44 | N | C—CF$_3$ | S | 4-SCH$_3$ | 3-Cl | $n_D^{20}$: 1.5475 |
| 45 | N | C—Cl | S | 4-OCH$_3$ | H | 88 |
| 46 | N | C—CF$_3$ | S | 4-OCH$_3$ | H | 76 |
| 47 | C—Cl | C—CHF$_2$ | S | 4-OCH$_3$ | H | $n_D^{20}$: 1.5262 |
| 48 | C—CHF$_2$ | C—Cl | S | H | H | 89 |
| 49 | N | C—CF$_3$ | S | 3-Cl | 5-Cl | 102 |
| 50 | C—CF$_3$ | N | S | 2-OCH$_3$ | H | 49 |
| 51 | C—CF$_3$ | N | S | 4-OC$_2$H$_5$ | H | 84 |
| 52 | C—CF$_3$ | N | S | 4-SCH$_3$ | 3-Cl | $n_D^{20}$: 1.5340 |

TABLE 2-continued

Preparation Examples of the compounds of the formula (I)

$$\underset{B-X}{\overset{A-N}{\|}}\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!}$$

(I)

with substituents A, B, X, $R^1$, $R^2$ on phenyl ring bearing CH(CH$_3$)$_2$ and O—CH$_2$—CO—N

| Ex. No. | A | B | X | $R^1$ | $R^2$ | Melting point (°C./ refractive index) |
|---|---|---|---|---|---|---|
| 53 | C—CF$_3$ | N | S | 4-OCH$_3$ | H | $n_D^{20}$: 1.5105 |
| 54 | N | C—CF$_3$ | S | 3-CH$_3$ | 5-CH$_3$ | 73 |
| 55 | N | C—CF$_3$ | S | 4-OCH$_3$ | 3-Cl | 81 |
| 56 | N | C—CF$_3$ | S | 3-Cl | 4-Cl | $n_D^{20}$: 1.5181 |
| 57 | N | C—CF$_3$ | S | 3-CF$_3$ | 5-CF$_3$ | 39 |
| 58 | C—CHF$_2$ | C—CF$_3$ | S | H | H | 50 |
| 59 | C—Cl | C—CHF$_2$ | S | 2-F | H | 86 |
| 60 | C—Cl | C—CHF$_2$ | S | 4-Cl | H | 66 |
| 61 | C—Cl | C—CHF$_2$ | S | 2-Cl | H | 76 |
| 62 | C—Cl | C—CHF$_2$ | S | 3-Cl | H | 68 |
| 63 | C—Cl | C—CHF$_2$ | S | 3-CH$_3$ | H | 75 |
| 64 | C—Cl | C—CHF$_2$ | S | 3-F | H | 87 |
| 65 | C—Cl | C—CHF$_2$ | S | 4-F | H | 67 |
| 66 | C—Cl | C—CHF$_2$ | S | 3-Cl | 4-Cl | 50 |
| 67 | C—Cl | C—CHF$_2$ | S | 4-OCH$_3$ | 3-Cl | 65 |
| 68 | C—Cl | C—CHF$_2$ | S | 4-OC$_2$H$_5$ | H | |
| 69 | C—Cl | C—CHF$_2$ | S | 3-CF$_3$ | 5-CF$_3$ | $n_D^{20}$: 1.4740 |
| 70 | C—Cl | C—CHF$_2$ | S | 2-CH$_3$ | 5-Cl | 100 |
| 71 | C—Cl | C—CHF$_2$ | S | 3-CH$_3$ | 5-CH$_3$ | 65 |
| 72 | C—Cl | C—CHF$_2$ | S | 3-Cl | 5-Cl | 81 |
| 73 | N | C—Cl | S | 3-CH$_3$ | 5-CH$_3$ | 118 |
| 74 | N | C—Cl | S | 3-Cl | 5-Cl | 102 |
| 75 | N | C—Cl | S | 4-OCH$_3$ | 3-Cl | 101 |
| 76 | N | C—Cl | S | 3-CF$_3$ | 5-CF$_3$ | 81 |
| 77 | N | C—Cl | S | 3-Cl | 4-Cl | 64 |
| 78 | N | C—Cl | S | 2-CH$_3$ | 5-Cl | 95 |
| 79 | N | C—CF$_3$ | S | 2-CH$_3$ | 5-Cl | 40 |
| 80 | C—CF$_3$ | N | S | 2-Cl | H | 74 |
| 81 | C—CF$_3$ | N | S | 3-F | H | 49 |
| 82 | C—CF$_3$ | N | S | 3-Cl | H | 58 |
| 83 | C—CF$_3$ | N | S | 4-F | H | 57 |
| 84 | C—CF$_3$ | N | S | 2-F | H | 67 |
| 85 | C—CF$_3$ | N | S | 4-Cl | H | $n_D^{20}$: 1.5165 |
| 86 | C—CF$_3$ | N | S | 3-CH$_3$ | H | $n_D^{20}$: 1.5041 |
| 87 | C—CF$_3$ | N | S | 3-CH$_3$ | 5-CH$_3$ | 54 |
| 88 | C—CF$_3$ | N | S | 3-Cl | 5-Cl | 53 |

STARTING SUBSTANCES OF THE FORMULA (III)

EXAMPLE (III-1)

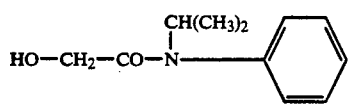

259 g (1.91 mol) of N-isopropylaniline are dissolved ion 2.2 l of toluene together with 182 g (2.29 mol) of pyridine. 259.7 g (1.91 mol) of acetoxyacetyl chloride are then added dropwise at 0°–5° C. Stirring is then continued for 1 hour at 0°–5° C. and for 12 hours at 20° C. For working up, the toluene phase is extracted by shaking with water and dilute hydrochloric acid, washed to neutrality using water, dried and concentrated. A crystalline beige-colored solid remains which melts at 101° C.

340 g (76% of theory) of N-isopropylacetoxyacetanilide are thus obtained.

Of this, 334 g (1.42 mol) are suspended in 500 ml of methanol. This suspension is introduced into a solution of 500 ml of water and 63 g of sodium hydroxide (1.57 mol). The mixture is stirred at 40° C. for 3 hours and then at 20° C. for another 12 hours. Using concentrated hydrochloric acid, the pH of the reaction solution is set at 6, and the solution is concentrated to half on a rotary evaporator. 500 ml of water are then added, and the reaction product is extracted using 700 ml of chloroform. The organic phase is washed with water, dried using sodium sulphate, filtered and evaporated.

256 g (94% of theory) of N-isopropylhydroxyacetanilide are thus obtained as a crystalline residue of melting point 39° C.

The compounds of the formula (III) which are listed in Table 3 below can also be prepared analogously to Example (III-1):

TABLE 3

Preparation Examples of compounds of the formula (III)

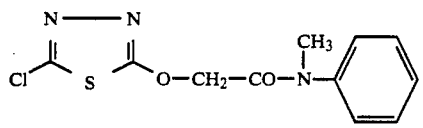

(III)

| Ex. No. | $R^1$ | $R^2$ | Melting point (boiling point) |
|---|---|---|---|
| (III-2) | 4-OCH₃ | H | 112° C. |
| (III-3) | 3-Cl | H | (b.p.: 140° C./1.3 Pa) |
| (III-4) | 4-Cl | H | 75° C. |
| (III-5) | 2-Cl | H | 50° C. |
| (III-6) | 2-F | H | 51° C. |

USE EXAMPLE

In the following Use Example, the compound of the formula below is used as comparison substance:

(A)

EXAMPLE A

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, for example the compounds of Preparation Examples: (1), (5) and (34) show a clear superiority with respect to selectivity in crop plants compared with the prior art.

It will be appreciated that the instant specification and claims are set forth by way of illustration and not limitation, and that various modifications and changes may be made without departing from the spirit and scope of the present invention.

What is claimed is:

1. An N-isopropyl-(1,2,4-thiadiazol-2-yl)oxyacetanilide of the formula

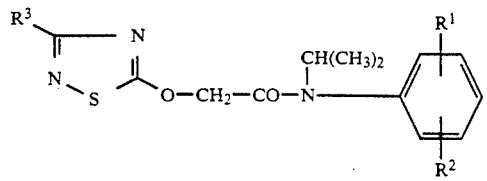

in which
R¹ stands for hydrogen, fluorine, chlorine, bromine, cyano, nitro, for $C_1-C_4$-alkyl which is optionally substituted by fluorine and/or chlorine, for $C_1-C_4$-alkoxy which is optionally substituted by fluorine and/or chlorine, or for $C_1-C_4$-alkylthio which is optionally substituted by fluorine and/or chlorine,
R² stands for hydrogen, fluorine, chlorine, bromine, methyl, trifluoromethyl or methoxy and
R³ stands for fluorine, chlorine, bromine, cyano, for $C_1-C_4$-alkyl which is optionally substituted by fluorine and/or chlorine, for $C_1-C_4$-alkoxy which is optionally substituted by fluorine and/or chlorine, for $C_1-C_4$-alkylthio which is optionally substituted by fluorine and/or chlorine, for $C_1-C_4$-alkylsulphinyl or $C_1-C_4$-alkylsulphonyl.

2. A compound according to claim 1, in which
R¹ stands for hydrogen, fluorine, chlorine, methyl, trifluoromethyl or methoxy,
R² stands for hydrogen, and
R³ stands for chlorine, difluoromethyl, trifluoromethyl, chlorodifluoromethyl, fluorodichloromethyl, dichloromethyl, trichloromethyl, methyl, ethyl, propyl, isopropyl, methylthio, ethylthio, propylthio, methylsulphonyl, ethylsulphonyl, propylsulphonyl, methylsulphinyl, ethylsulphinyl or propylsulphinyl.

3. A compound according to claim 1, wherein such compound is N-isopropyl-(5-dichlorofluoromethyl-1,3,4-thiadiazol-2-yl)-oxyacetanilide of the formula

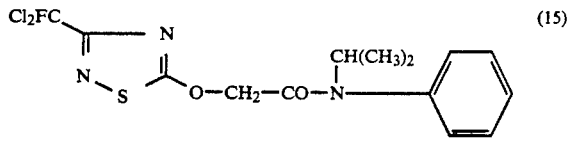

(15)

4. A compound according to claim 1, wherein such compound is N-isopropyl-(5-trifluoromethyl-1,3,4-thiadiazol-2-yl)-oxyacetanilide of the formula

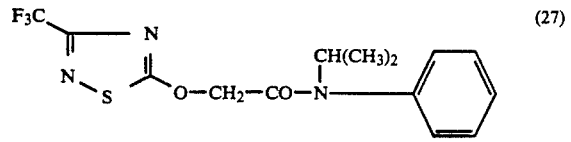

(27)

5. A compound according to claim 1, wherein such compound is N-isopropyl-(5-trifluoromethyl-1,3,4-thiadiazol-2-yl)-(4'-fluoro-oxyacetanilide) of the formula

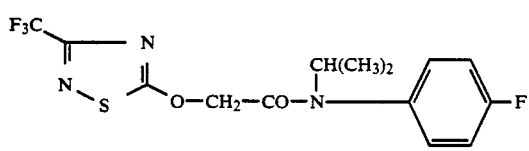 (83)

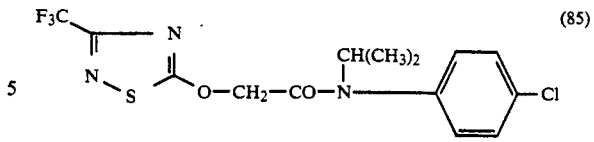 (85)

6. A compound according to claim 1, wherein such compound is N-isopropyl-(5-trifluoromethyl-1,3,4-thiadiazol-2-yl)-(2'-fluoro-oxyacetanilide) of the formula

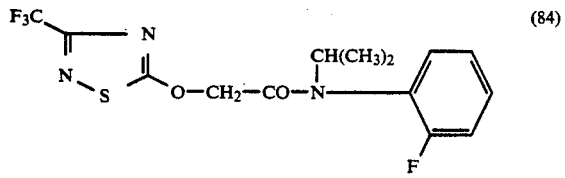 (84)

7. A compound according to claim 1, wherein such compound is N-isopropyl-(5-trifluoromethyl-1,3,4-thiadiazol-2-yl)-(4'-chloro-oxyacetanilide) of the formula 8. A herbicidal composition comprising a herbicidally effective amount of a compound according to claim 1 and a diluent.

9. A method of combating unwanted vegetation which comprises applying to such vegetation or to a locus from which it is desired to exclude such vegetation a herbicidally effective amount of a compound according to claim 1.

10. The method according to claim 9, wherein such compound is
N-isopropyl-(5-dichlorofluoromethyl-1,3,4-thiadiazol-2-yl)-oxyacetanilide,
N-isopropyl-(5-trifluoromethyl-1,3,4-thiadiazol-2-yl)-oxyacetanilide,
N-isopropyl-(5-trifluoromethyl-1,3,4-thiadiazol-2-yl)-(4'-fluoro-oxyacetanilide),
N-isopropyl-(5-trifluoromethyl-1,3,4-thiadiazol-2-yl)-(2'-fluoro-oxyacetanilide) or
N-isopropyl-(5-trifluoromethyl-1,3,4-thiadiazol-2-yl)-(4'-chloro-oxyacetanilide).

* * * * *